United States Patent [19]
Harris et al.

[11] 3,991,194
[45] Nov. 9, 1976

[54] HETEROCYCLIC ESTERS OF BENZOPYRANOPYRIDINES

[75] Inventors: Louis Selig Harris, Chapel Hill, N.C.; Harry George Pars, Lexington, Mass.; John Clark Sheehan, Lexington, Mass.; Raj Kumar Razdan, Belmont, Mass.

[73] Assignee: Sharps Associates, Cambridge, Mass.

[22] Filed: Dec. 4, 1972

[21] Appl. No.: 311,953

Related U.S. Application Data

[63] Continuation-in-part of Ser. No. 212,819, Dec. 27, 1971, abandoned.

[52] U.S. Cl. .......................... 424/246; 260/240 R; 260/240 D; 260/240 K; 260/243 B; 260/247.2 B; 260/268 TR; 260/293.58; 260/295 T; 424/248; 424/250; 424/263; 424/267

[51] Int. Cl.² ........................... C07D 491/04

[58] Field of Search ........ 260/240 R, 240 D, 240 K, 260/247.2 B, 268 TR, 293.55, 293.58, 295 T, 297 T, 345.3, 243 B; 424/246, 248, 250, 263, 267

[56] References Cited
UNITED STATES PATENTS

| | | | |
|---|---|---|---|
| 3,452,046 | 6/1969 | Yale et al. .......................... | 260/327 |
| 3,509,163 | 4/1970 | Brandstrom et al. ............. | 260/94.7 |
| 3,514,464 | 5/1970 | Pars et al. .......................... | 260/295 |
| 3,522,260 | 7/1970 | Shulgin ............................. | 260/294.3 |
| 3,542,789 | 11/1970 | Satzinger ......................... | 260/293.4 |
| 3,656,906 | 4/1972 | Bullock ............................. | 23/230 B |
| 3,728,360 | 4/1973 | Pars et al. .......................... | 260/345.3 |
| 3,787,424 | 1/1974 | Pars et al. .......................... | 260/295 |

OTHER PUBLICATIONS

Buzas et al., Compt. Rend. 256, 1804–1806, (1963).

*Primary Examiner*—G. Thomas Todd
*Attorney, Agent, or Firm*—Merriam, Marshall, Shapiro & Klose

[57] ABSTRACT

Novel heterocyclic esters of benzopyranopyridines represented by the formula

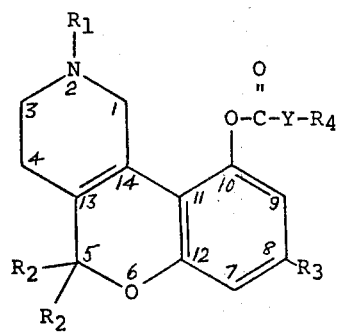

wherein $R_1$ is hydrogen, lower alkyl, lower alkanoyl, cycloalkyl-lower alkyl, cycloalkyl-lower alkanoyl, lower alkenyl, lower alkynyl, halo-loweralkenyl, phenyl-lower alkyl, phenyl-lower alkenyl or phenyl-lower alkynyl; $R_2$ is lower alkyl; $R_3$ is an alkyl having one to twenty carbon atoms or a cycloalkyl-lower alkyl, Y is a straight or branched chain alkylene having one to eight carbon atoms, and $R_4$ is a group of the formula

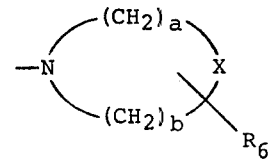

$a$ is an integer from 1 to 4, $b$ is an integer from 1 to 4 and X is $CH_2$, O, S or $N-R_5$ with $R_5$ being hydrogen or lower alkyl, with the limitation that when X is O, S or $N-R_5$, $a$ and $b$ each must be 2 and $R_6$ is hydrogen or a lower alkyl group bonded to a carbon in the ring; and the acid addition salts thereof.

21 Claims, No Drawings

HETEROCYCLIC ESTERS OF BENZOPYRANOPYRIDINES

CROSS-REFERENCE TO RELATED APPLICATION

This application is a continuation-in-part of our co-pending patent application Ser. No. 212,819, filed Dec. 27, 1971 and now abandoned.

DETAILED DESCRIPTION OF THE INVENTION

This invention relates to novel heterocyclic esters of benzopyranopyridines, to methods of preparing the compounds, to pharmaceutical compositions containing the compounds and to use of the compounds and pharmaceutical compositions containing the compounds for pharmacological and medicinal purposes.

According to one aspect of this invention compounds are provided which can be represented by the formula

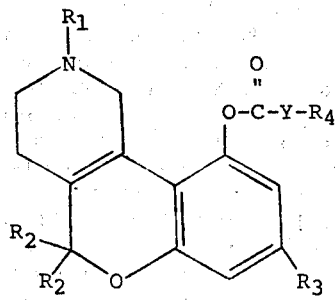

Formula 1 wherein $R_1$ is hydrogen, lower alkyl, lower alkanoyl, cycloalkyl-lower alkyl, cycloalkyl-lower alkanoyl, lower-akenyl, lower-alkynyl, halo-lower-alkenyl, phenyl-lower alkyl, phenyl-lower alkenyl or phenyl-lower alkynyl; $R_2$ is lower alkyl; $R_3$ is an alkyl having one to twenty carbon atoms or cycloalkyl-lower alkyl, Y is a straight or branched chain alkylene having one to eight carbon atoms, and $R_4$ is a group of the formula

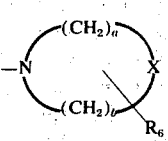

wherein $a$ is an integer from 1 to 4, $b$ is an integer from 1 to 4 and X is $CH_2$, O, S or N—$R_5$, $R_5$ being hydrogen or lower alkyl, with the limitation that when X is O, S or N—$R_5$, $a$ and $b$ each must be 2 and $R_6$ is hydrogen or a lower alkyl group bonded to a carbon in the ring; and the acid addition salts thereof.

The term lower alkyl as used herein, refers to $C_1$–$C_6$ straight or branched chain alkyl groups including methyl, ethyl, n-propyl, iso-propyl, n-butyl, sec-butyl, tert-butyl, n-pentyl, iso-pentyl, neo-pentyl, n-hexyl and the like.

The term lower alkenyl refers to straight and branched chain $C_2$–$C_6$ alkyl radicals from which a hydrogen atom has been removed from each of two adjacent carbon atoms to produce ethylenic unsaturation; e.g., vinyl, allyl, methallyl, 1-pentenyl and the like.

The term lower alkynyl refers to $C_2$–$C_6$ alkyl groups as defined above, from which two hydrogen atoms have been removed from each of two adjacent carbon atoms to produce acetylenic unsaturation; e.g., ethynyl, propargyl, 2-butynyl, 1-pentynyl and the like groups.

The term halo includes chloro, fluoro, bromo and iodo.

The term lower alkanoyl refers to saturated, monovalent, aliphatic radicals derived from a monocarboxylic acid, including straight or branched chain radicals of from one to six carbon atoms including the formyl, acetyl, propionyl, α-methylpropionyl, butyryl, hexanoyl and the like radicals.

Cycloalkyl, as used herein, refers to cyclic, saturated aliphatic radicals having three to eight carbon atoms in a ring, such as cyclopropyl, cyclobutyl, cyclopentyl, cyclohexyl, cycloheptyl and cyclooctyl.

Cycloalkyl-lower alkyl refers to groups such as cyclopropyl-methyl, 2-methylcyclobutyl and the like.

The term alkyl refers to straight and branched chain alkyl radicals having from one to twenty carbon atoms such as methyl, n-amyl, 3-methyl-2-octyl, 2-nonyl, 2-eicosanyl and the like.

The term acid addition salts refers to non-toxic salts prepared by reacting the basic esters of the benzopyranopyridines with an organic or inorganic acid, or by reacting the benzopyranopyridines with the salt of an appropriate acid. Representative salts include the hydrochloride, hydrobromide, sulfate, bisulfate, acetate, valerate, oleate, laurate, borate, benzoate, lactate, phosphate, tosylate, citrate, maleate, succinate, tartrate, napsylate and the like. Such salts are well known in the art and are considered to be pharmaceutically acceptable.

The compounds provided by the invention considered particularly useful are those of the formula

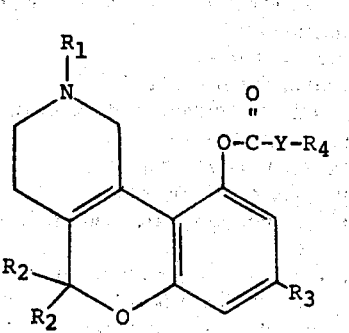

Formula 2 in which $R_1$ is a lower alkynyl, each $R_2$ is methyl, $R_3$ is an alkyl group having five to nine carbon atoms, Y is a branched or straight chain alkylene having 2 to 5 carbon atoms and, in the groups represented by $R_4$ in Formula 1, $a$ and $b$ are the same or different integers from 1 to 3 and $a + b$ is an integer from 3 to 5, $R_6$ is hydrogen or lower alkyl, and X is $CH_2$ or 0. The preferred compounds are those in which $R_1$ is propargyl, $R_3$ is 3-methyl-2-octyl or pentyl and the sum of $a + b$ is 3 or 4.

Generally speaking, the esters of this invention are prepared by reacting equimolar quantities of the corresponding benzopyranopyridines, and the appropriate acid or its salt, in the presence of a carbodiimide, such as dicyclohexylcarbodiimide, in a suitable solvent such as methylene chloride, chloroform and the like. This reaction can be represented as follows:

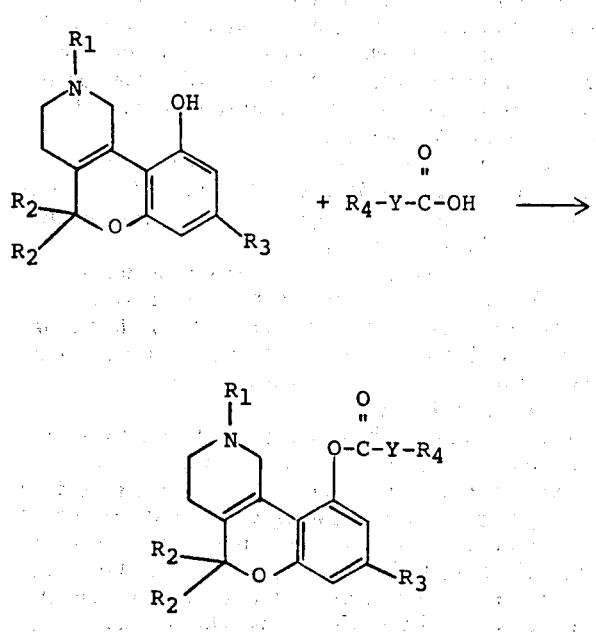

wherein $R_1$, $R_2$, $R_3$, $R_4$ and Y are defined above.

The benzopyranopyridine starting compounds and their preparation are disclosed in U.S. Pat. No. 3,576,798.

Some of the heterocyclic acids which can be used in the process are:
γ-piperidinobutyric acid,
γ-morpholinobutyric acid,
γ-(2-methylpiperidino)-butyric acid,
δ-piperidinovaleric acid,
γ-pyrrolidinobutyric acid,
β-piperidinopropionic acid,
γ-thiomorpholinobutyric acid and homopiperidinoacetic acid Reaction between the benzopyranopyridine starting material and the heterocyclic acid, or salt thereof, is readily effected by combining about equimolar amounts of the reactants and a slight excess of a carbodiimide such as dicyclohexylcarbodiimide. The reaction proceeds readily at room temperature and is generally completed in about 4 to 20 hours. After the reaction is terminated, the reaction mixture can be filtered to remove the by-product of dicyclohexylurea, and the solvent can be distilled off using a rotary evaporator. The residue can be directly crystallized from a suitable solvent such as benzene/ether or the residue can be chromatographed and the desired material isolated from the appropriate chromatographic fractions. If the basic esters are obtained, the acid addition salts such as those named above, if desired, can be prepared by methods well known in the art.

The compounds of this invention, in the form of the free bases, can be used as neutralizing agents since they form salts with acids.

The pharmacological activity of the compounds of this invention renders them useful as drugs although it should be understood that every compound of the invention will not necessarily have each activity possessed by the others.

The compounds of this invention are useful as analgesic agents, and generally at dosages of from 5 to 20 mg./kg. of body weight daily. In test animals, the compounds appear to be in the potency range of α-d-propoxyphene and codeine. The analgesic activity was first established in the rat tail flick method of Harris et al J.P.E.T., 169, 17 (1969) and the well-known acetic acid writhing and hot plate tests.

The compounds additionally exhibit mild tranquilizing activity in test animals, and generally at dosages of from 0.1 to 20 mg./kg. of body weight.

The compounds also exert anticonvulsant activity and sedative-hypnotic activity in animals.

The amount of active ingredient administered may be varied; however, it is necessary that the amount of active ingredient be such that a suitable dosage is given. The selected dosage depends upon the desired therapeutic effect, on the route of administration and on the duration of treatment. In general, if only tranquilization is desired, dosages of from 0.1 to 10 mg./kg. of body weight daily is administered, preferably in divided doses, i.e., three to four times daily. If analgesia is also desired, then dosages generally of from 5 to 20 mg./kg. of body weight is administered daily, again, preferably in divided doses.

Specific activity for some of the compounds of the invention will now be presented.

The compound of Example 1 (SP-106) is a tranquilizing agent in mice at 5 to 10 mg./kg. orally; an analgesic agent at 4 to 12 mg./kg. orally in mice and rats; and a sedative-hypnotic agent in cats and monkeys at 0.5 to 1.0 mg./kg. orally.

The compound of Example 2 (SP-112) is a tranquilizing agent in mice at 5 to 10 mg./kg. orally; an analgesic agent in mice and rats at 9 to 12 mg./kg. orally; and a sedative-hypnotic agent at 1 mg./kg. orally in cats and monkeys.

The compound of Example 3 (SP-159) is a tranquilizing agent in mice at 10 mg./kg. orally and it is an anticonvulsant agent in mice at 30 mg./kg. orally.

The compound of Example 4 (SP-158) is a tranquilizing agent in mice at 10 mg./kg. orally and it is an anticonvulsant agent in mice at 30 mg./kg. orally.

The compound of Example 5 (SP-167) is a tranquilizing agent in mice at 10 mg./kg. orally and it is an anticonvulsant agent in mice at 30 mg./kg. orally.

The compound of Example 6 (SP-171) is a tranquilizing agent in mice at 5 mg./kg. orally.

The compound of Example 8 (SP-178) is a tranquilizing agent in mice at 10 mg./kg. orally.

The active agents of this invention can be administered to animals, including humans, as pure compounds. It is advisable, however, to first combine one or more of the compounds with a suitable pharmaceutical carrier to attain a satisfactory size to dosage relationship and thereby obtain a pharmaceutical composition.

Pharmaceutical carriers which are liquid or solid can be used. Solid carriers such as starch, sugar, talc and the like can be used to form powders. The powders can be used for direct administration or they may be used to make tablets or to fill gelatin capsules. Suitable lubricants like magnesium stearate, binders such as gelatin, and disintegrating agents like sodium carbonate in combination with citric acid can be used to form tablets. Sweetening and flavoring agents can also be included.

Unit dosage forms such as tablets and capsules can contain any suitable predetermined amount of one or more of the active agents, and they may be administered one or more at a time at regular intervals. Such unit dosage forms, however, should generally contain a concentration of 0.1 to 50 percent by weight of one or more of the active compounds. Unit dosage forms, such as tablets and capsules, can contain about 5 to 300 mg. of active agent.

A typical tablet can have the composition:

| | Mg |
|---|---|
| Active agent[1] | 100 |
| Starch U.S.P. | 57 |
| Lactose U.S.P. | 73 |
| Talc. U.S.P. | 9 |
| Stearic acid | 12 |

[1]Any compound from Examples 1 to 19 can be the active agent.

The compounds of this invention exhibit both oral and parenteral activity and accordingly can be formulated in dosage forms for either oral or parenteral administration to a patient.

Solid dosage forms for oral administration include capsules, tablets, pills, powders, granules and the like.

Liquid dosage forms for oral administration include emulsions, solutions, suspensions, syrups and the like, containing diluents commonly used in the art such as water. Besides inert diluents, such preparations can also include adjuvants such as wetting agents, emulsifying and suspending agents and sweetening, flavoring and perfuming agents.

Preparations for parenteral administration include sterile aqueous or non-aqueous solutions. Examples of non-aqueous solvents or vehicles are propylene glycol, polyethylene glycol, vegetable oils such as olive oil and injectable organic esters such as ethyl oleate. The parenteral preparations are sterilized by conventional methods.

The following examples are presented to further illustrate the invention.

EXAMPLE 1

5,5-Dimethyl-8-(3-methyl-2-octyl)-10-[4-(piperidino)-butyryloxy-2-(2-propynyl)-1,2,3,4-tetrahydro-5H-[1]benzopyrano[3,4-d]pyridine hydrochloride (SP-106)

4.5 g. (11.4 mm.) of 5,5-Dimethyl-10-hydroxy-8-(3-methyl-2-octyl)-2-(2-propynyl)-1,2,3,4-tetrahydro-5H-[1] benzopyrano [3,4-d] pyridine, 258 g. (12.5 mm.) of dicyclohexylcarbodiimide and 2.49 g. (12.0 mm.) of γ-piperidinobutyric acid hydrochloride (Cruickshank and Sheehan, J. Am. Chem. Soc., 83, 2891 (1961) m.p. 190°–192° C) were combined in 250 ml. of methylene chloride and stirred at room temperature for 16 hours. The insoluble by-product of dicyclohexylurea was separated by filtration and the methylene chloride was removed using a rotary evaporator. The residue was dissolved in benzene or benzene/cyclohexane mixtures and filtered several times to remove a small amount of insoluble material. The solvent was evaporated and the residue was dissolved in water and lyophilized to give 2.3 g. (37%) of the product as a light yellow solid.

The material showed an $R_f$ of 0.5 in thin layer chromatography (10% MeOH/CHCl$_3$); the infrared and nuclear magnetic resonance spectra were in agreement with the proposed structure.

Analysis Calcd. for $C_{35}H_{53}ClN_2O_3$ . 2½ H$_2$O (MW=630.27): C, 66.70; H, 9.29; N, 4.46; Found: C, 66.58; H, 8.93; N, 4.54.

EXAMPLE 2

5,5-Dimethyl-10-[4-(morpholino)butyryloxy]-8-(3-methyl-2-octyl)2-(2-propynyl)-1,2,3,4-tetrahydro-5H-[1] benzopyrano [3,4-d] pyridine hydrochloride (SP-112)

0.6 g. (1.51 mm.) of 5,5-Dimethyl-10-hydroxy-8-(3-methyl-2-octyl)-2-(2-propynyl)-1,2,3,4-tetrahydro-5H-[1]benzopyrano [3,4-d]pyridine, 0.317 g. (1.51 mm.) of γ-morpholinobutyric acid hydrochloride (Cruickshank and Sheehan, J.A.C.S. 83, 2891 (1961) and 0.34 g. (1.65 mm.) of dicyclohexylcarbodiimide were combined in 40 ml. of methylene chloride and stirred for 16 hours at room temperature. The insoluble by-product of dicyclohexylurea was removed by filtration and the methylene chloride was distilled off using a rotary evaporator. The residue was dissolved in a small amount of benzene and ether was added to give 0.4 g. of material. Recrystallization from methylene chloride/ligroin (b.p. 100°–115° C) gave 0.3 g. (31%) of product as a beige solid, mp. 158°–161° C. The sample was found pure by thin layer chromatography (20% MeOH/CHCl$_3$). The infrared and nuclear magnetic resonance spectra are consistent with the proposed structure.

Analysis Calcd. for $C_{34}H_{51}ClN_2O_4$ . 2½ H$_2$O (MW=632.26): C, 64.60; H, 8.93; N, 4.43; Found: C, 64.32; H, 8.54; N, 4.31.

EXAMPLE 3

5,5-Dimethyl-10-[4-(2-methylpiperidino) butyryloxy]-8-(3-methyl-2-octyl)-2-(2-propynyl)-1,2,3,4-tetrahydro-5H-[1]benzopyrano [3,4-d] pyridine hydrochloride (SP-159)

14.0 g. (0.07 mole) of methyl γ-(2-methylpiperidino) butyrate was dissolved in 180 ml. of 18% hydrochloric acid solution (90 ml. water and 90 ml. concentrated hydrochloric acid) and refluxed for 16 hours. The excess water was removed using reduced pressure (water aspirator) to give a semi-solid residue which was triturated with acetone and filtered. 11.3 g. (73%) of γ-(2-methylpiperidino) butyric acid hydrochloride was obtained as colorless crystals, m.p. 180°–182° C.

A mixture of 3.0 g. (7.6 mm.) of 5,5-dimethyl-10-hydroxy-8-(3-methyl-2-octyl)-2-(2-propynyl)-1,2,3,4-tetrahydro5H-[1] benzopyrano [3,4,-d]pyridine, 1.68 g. (7.6 mm.) of γ-(2-methylpiperidino)butyric acid hydrochloride and 1.65 g. (8.0 mm.) of dicyclohexylcarbodiimide in 150 ml. of methylene chloride was stirred at room temperature for 16 hours. The reaction mixture was cooled and the solid removed by suction filtration. The methylene chloride was evaporated to give a residue which was dissolved in 8 ml. of methylene chloride and 58 ml. of diethyl ether. After standing for 3 days, a total of 100 mg. of solid was removed by gravity filtration. The solvents were evaporated and the gummy resin was dried to give a foam-like residue which was triturated with 30 ml. of diethyl ether. The resulting nearly colorless, gummy residue was dried to give 2.8 g. (61%) of tan solid.

The sample was pure by thin layer chromatography (5% MeOH/CHCl$_3$); the infrared and nuclear magnetic resonance spectra were in agreement with the proposed structure.

Analysis Calcd. for $C_{36}H_{55}ClN_2O_3$ (MW=599.28): C, 72.14; H, 9.25; N, 4.67; Found: C, 71.94 H, 9.16; N, 4.58.

EXAMPLE 4

5,5-Dimethyl-10-[5-(piperidino)valeryloxy]-8-(3-methyl-2-octyl)2-propynyl)-1,2,3,4-tetrahydro-5H-[1]benzopyrano[3,4-d] pyridine hydrochloride (SP-158)

A mixture of 25.0 g. (0.167 mole) of methyl δ-chlorovalerate and 37.5 g. (0.25 mole) of sodium iodide in 120 ml. of acetone was stirred and heated at reflux for 16 hours. After cooling the mixture, a solid was removed by suction filtration, and the acetone was distilled off using a rotary evaporator. The residue was dissolved in 300 ml. of diethyl ether, and additional solid was removed by filtration. The ethereal solution was washed twice with a 10% sodium thiosulfate solution, once with water and dried over sodium sulfate. The ether was evaporated and the residue distilled at b.p. 107°–110° C (15 mm.) to give 30.0 g. (74%) of methyl δ-iodovalerate as a light yellow liquid.

30.0 g. (0.124 mole) of methyl δ-iodovalerate and 42.5 g. (0.50 mole) of piperidine were dissolved in 250 ml. of benzene and heated at 60° C for 3 hours with stirring. A colorless solid began to appear shortly after the materials were combined. The solid was removed by suction filtration, and the benzene evaporated to give methyl δ-piperidinovalerate which distilled as 23.5 g. (95%) of colorless liquid, b.p. 122°–24° C (12.5 mm.).

23.5 g. (0.117 mole) of methyl δ-piperidinovalerate was dissolved in a combination of 125 ml. of concentrated hydrochloric acid and 125 ml. of water and refluxed with stirring for 16 hours. The excess water was removed using reduced pressure (water aspirator) to give a semi-solid residue which was triturated with acetone, filtered and dried. 21.0 g. (79%) of colorless crystals of δ-piperidinovaleric acid hydrochloride was obtained with a m.p. of 202°–204° C.

A mixture of 2.4 g. (6.06 mm.) of 5,5-dimethyl-10-hydroxy-8-(3-methyl-2-octyl)-2-(2-propynyl)-1,2,3,4-tetrahydro5H-[1]benzopyrano[3,4-d]pyridine, 1.35 g. (6.06 mm.) of δ-piperidinovaleric acid hydrochloride and 1.30 g. (6.30 mm.) of dicyclohexylcarbodiimide in 100 ml. of methylene chloride was stirred at room temperature for 5 hours. The reaction mixture was cooled overnight in the refrigerator and the byproduct of dicyclohexylurea removed by suction filtration. The mother liquor was evaporated to give a golden, viscous residue which was dissolved in a mixture of methylene chloride/cyclohexane and allowed to stand in the cold for 2 hours. Gravity filtration separated a small amount of solid which had appeared, and the solvents were removed using a rotary evaporator. Crystallization from methylene chloride/diethyl ether gave 2.5 g. (69%) of colorless crystals, m.p. 140°–144° C. The sample was pure by thin layer chromatography (10% MeOH/CHCl$_3$) and the infrared and nuclear magnetic resonance spectra were in agreement with the proposed structure.

Analysis Calcd. for $C_{36}H_{55}ClN_2O_3$ (MW=599.28): C, 72.14; H, 9.25; N, 4.67; Found: C, 72.00; H, 9.11; N, 4.63.

EXAMPLE 5

5,5-Dimethyl-10-[4-pyrrolidino)butyryloxy]-8-(3-methyl-2-octyl)2-(2-propynyl)-1,2,3,4-tetrahydro-5H-[1]benzopyrano[3,4-d]pyridine dihydrochloride (SP-167)

30.0 g. (0.13 mole) of methyl δ-iodobutyrate [Blicke et al, *J. Am Chem. Soc.*, 63, 2488 (1941)] was combined with 36 g. (0.5 mole) of pyrrolidine in 300 ml. of benzene and heated at 60° C for 0.5 hour and stirred at room temperature for 16 hours. A dark orange layer formed, and the benzene solution was decanted, concentrated and distilled to give 10 g. of colorless liquid. This material was dissolved in a combination of 50 ml. of concentrated hydrochloric acid and 50 ml. of water and heated at reflux for 28 hours. The solution was concentrated under reduced pressure to give a semisolid residue which was triturated with acetone and filtered. Recrystallization from a combination of 11 ml. of acetic acid/40 ml. of acetone gave 8.3 g. (33%) of colorless crystals of γ-pyrrolidinobutyric acid hydrochloride, m.p. 126°–127° C.

3.0 g. (7.57 mm.) of 5,5-dimethyl-10-hydroxy-8-(3-methyl-2-octyl)-2-(2-propynyl)-1,2,3,4-tetrahydro-5H-[1]benzopyran[3,4-d]pyridine was combined with 1.45 g. (7.57 mm.) of γ-pyrrolidinobutyric acid hydrochloride and 1.67 g. (8.12 mm.) of dicyclohexylcarbodiimide in 150 ml. of methylene chloride and stirred at room temperature for 3 hours. The reaction mixture was stored for 16 hours in the cold, and the byproduct of dicyclohexylurea was removed by suction filtration. After evaporation of the solvents, the resulting gummy residue was dissolved in a mixture of 25 ml. of methylene chloride and 65 ml. of cyclohexane and allowed to stand at room temperature for 2 hours and at 5° C for 16 hours. A small quantity of solid was separated by gravity filtration, and the solvents were removed on a rotary evaporator. Crystallation from methylene chloride and diethyl ether gave 0.75 g. (16%) of the desired product as the dihydrochloride, a colorless solid having a melting point of 168°–171° C which was pure by thin layer chromatography (10% MeOH/CHCl$_3$). The infrared and nuclear magnetic resonance spectra were in agreement with the proposed structure.

Analysis Calcd. for $C_{34}H_{52}Cl_2N_2O_3 \cdot H_2O$ (MW=624.70): C, 65.35; H, 8.54; N, 4.48; Found: C, 65.24; H, 8.32; N, 4.58.

EXAMPLE 6

5,5-Dimethyl-10-[4-(piperidino)butyryloxy]-2-(2-propynyl)-8-pentyl-1,2,3,4-tetrahydro-5H-[1]benzopyrano[3,4-d]pyridine hydrochloride (SP-171)

A mixture of 1.45 g. (4.26 mm.) of 5,5-dimethyl-10-hydroxy-2-(2-propynyl)-8-pentyl-1,2,3,4-tetrahydro-5H-[1]benzopyrano[3,4-d]pyridine, 0.89 g. (4.28 mm.) of γ-piperidinobutyric acid hydrochloride and 0.93 g. (4.50 mm.) of dicyclohexylcarbodiimide in 200 ml. of methylene chloride was stirred at room temperature for 18 hours. After cooling the reaction mixture for 1½ hours, the byproduct of dicyclohexylurea was removed by suction filtration. A rotary evaporator was used to remove the methylene chloride, and a mixture of 25 ml. of methylene chloride and 50 ml. of cyclohexane was added. After standing at room temperature for 2 hours and at 5° C for 16 hours, gravity filtration was used to separate 300 mg. of solid. This material proved to be a mixture of the starting acid hydrochloride and the hydrochloride salt of the starting benzopyran. The mother liquor was evaporated and the residue was crystallized from a mixture of 2 ml. of methylene chloride and 15 ml. of diethyl ether. After filtration and drying, a total of 0.5 g. (22%) of colorless solid was obtained. The sample was pure by thin layer chromatography (10% MeOH/CHCl$_3$). The infrared and nuclear magnetic resonance spectra were in agreement with the proposed structure.

Analysis Calcd. for $C_{31}H_{45}ClN_2O_3 \cdot 1/2H_2O$ (MW=538.15): C, 69.18; H, 8.61; N, 5.20;. Found: C, 69.08; H, 8.74; N, 5.20.

EXAMPLE 7

5,5-Dimethyl-8-(3-methyl-2-octyl)-10-[4-(piperidino)-butyryloxy]-2-(2-propynyl)-1,2,3,4-tetrahydro-5H-[1]benzopyrano[3,4-d] pyridine hydrochloride (SP-106)

The preparation of this compound was repeated by combining equimolar quantities of 5,5-dimethyl-10-hydroxy-8-(3-methyl-2-octyl)-2-(2-propynyl)-1,2,3,4-tetrahydro-5H-[1]benzopyrano[3,4-d]pyridine, dicyclohexylcarbodiimide and γ-piperidinobutyric acid hydrochloride in methylene chloride. After stirring for about 16 hours at room temperature, the reaction mixture was cooled, and the byproduct of dicyclohexylurea was removed by suction filtration. The mother liquor was evaporated to give a light yellow residue which was dissolved in a methylene chloride/cyclohexane mixture and stored in the cold for 16 hours. A small quantity of additional dicyclohexylurea was removed by filtration, and the solvents were distilled off using a rotary evaporator. The residue which remained was dried in vacuo and crystallized from a mixture of methylene chloride and diethyl ether to give a colorless solid, m.p. 108°–111° C. Thin layer chromatography (10% MeOH/CHCl$_3$) indicated the compound to be pure; the nuclear magnetic resonance and infrared spectra of the material were consistent with the desired product.

Analysis Calcd. for $C_{35}H_{53}ClN_2O_3$ (MW=585.24): C, 71.80; H, 9.12; N, 4.78; Found: C, 71.82; H, 9.17; N, 4.85.

A second crop of material was obtained by workup of the mother liquor, and this material appeared similar to the main batch in all ways.

Analysis: Found: C, 71.66; H, 9.05; N, 4.76. Total yield for both batches was 95%.

EXAMPLE 8

5,5-Dimethyl-10-[2-methyl-4-(piperidino)butyryloxy]-8-(3-methyl-2-octyl)-2-(2-propynyl)-1,2,3,4-tetrahydro-5H-[1]benzopyrano[3,4-d] pyridine dihydrochloride (SP-178)

The method of Lee V. Phillips (U.S. Pat. No. 3,299,100) was used to prepare α-methyl-γ-butyrolactone and this material was converted to ethyl γ-bromo-α-methylbutyrate via the procedure of G. Jones and J. Wood, "The Synthesis of 9-Azasteroids-II", *Tetrahedron*, 21, 2961 (1965).

10.5 g. (0.05 mole) of ethyl γ-bromo-α-methylbutyrate was combined with 17.0 g. (0.20 mole) of piperidine and 100 ml. of benzene and stirred for 16 hours at room temperature and heated at 60° C for 4 hours. The reaction mixture was cooled and the colorless solid which appeared was removed by filtration. The mother liquor was concentrated to give ethyl α-methyl-γ-piperidinobutyrate as a mobile yellow liquid which distilled (b.p. 78° C at 0.25 mm.) as 6.7 g. (63%) of colorless liquid. The nuclear magnetic resonance and infrared spectra were consistent with the desired compound.

6.5 g. (0.030 mole) of ethyl α-methyl-γ-piperidinobutyrate was combined with a mixture of 45 ml. of water and 45 ml. of concentrated hydrochloric acid and heated at reflux for 16 hours. The solution was concentrated under reduced pressure (water aspirator) to give a residue which crystallized upon addition of 50 ml. of diethyl ether. The ether was decanted, and the solid was triturated with acetone and filtered. Recrystallization from acetic acid/acetone gave 3.38 g. of α-methyl-γ-piperidinobutyric acid hydrochloride as colorless crystals, m.p. 166°–68° C and a second crop of 1.27 g. of solid, m.p. 165°–168° C. The total yield for both batches was 69%. The nuclear magnetic resonance and infrared spectra were in agreement with the proposed structure.

2.0 g. (5.05 mm.) of 5,5-dimethyl-10-hydroxy-8-(3-methyl-2-octyl)-2-(2-propynyl)-1,2,3,4-tetrahydro-5H-[1] benzopyrano[3,4-d] pyridine was combined with 1.12 g. (5.05 mm.) of α-methyl-γ-piperidino butyric acid hydrochloride and 1.08 g. (5.25 mm.) of dicyclohexylcarbodiimide in 110 ml. of methylene chloride and the mixture was stirred at room temperature for 16 hours. After cooling for 4 hours, the byproduct of dicyclohexylurea was removed by suction filtration. The mother liquor was evaporated to give a colorless foamy residue which was dissolved in a methylene chloride/cyclohexane mixture and stored for 16 hours in the cold. A small amount of solid was separated by gravity filtration, and the solvents were removed using a rotary evaporator. The residue was dried to give 2.6 g. of colorless solid which was combined with 0.6 g. of material obtained from an earlier preparation. Both samples were dissolved in a mixture of methylene chloride/diethyl ether and converted to the dihydrochloride by the addition of a solution of hydrogen chloride in diethyl ether. The solvents were decanted, and the gummy residue crystallized upon trituration with diethyl ether. The solid was filtered and recrystallized from 20 ml. of methylene chloride/20 ml. diethyl ether to give 1.7 g. of 5,5-dimethyl-10-[2-methyl-4-(piperidino)butyryloxy]-8-(3-methyl-2-octyl)-2-(2-propynyl)-1,2,3,4-tetrahydro-5H-[1] benzopyrano[3,4-d]pyridine dihydrochloride as colorless crystals, m.p. 175°–80° C. The nuclear magnetic resonance and infrared spectra were consistent with the desired structure, and the material was pure by thin layer chromatography (10% MeOH/CHCl₃).

Analysis Calcd. for $C_{36}H_{56}Cl_2N_2O_3$ (MW=635.74): Theory: C, 68.00; H, 8.88; N, 4.41; Found: C, 67.96; H, 8.70; N, 4.34.

EXAMPLE 9

5,5-Dimethyl-10-[4-(morpholino)butyryloxy]-8-(3-methyl-2-octyl)2-(2-propynyl)-1,2,3,4-tetrahydro-5H-[1]benzopyrano[3,4-d]pyridine dihydrochloride (SP-112)

4.0 g. (10.1 mm.) of 5,5-dimethyl-10-hydroxy-8-(3-methyl-2-ocytyl)-2-(2-propynyl)-1,2,3,4-tetrahydro-5H-[1]benzopyrano[3,4-d]pyridine, 2.10 g. (10.1 mm.) of γ-morpholinobutyric acid hydrochloride and 2.18 g. (10.6 mm.) of dicyclohexylcarbodiimide were added to 200 ml. of methylene chloride. The reaction mixture was stirred at room temperature for 16 hours and after cooling the byproduct of dicyclohexylurea was removed by suction filtration. The mother liquor was evaporated to give a residue which after the usual workup was converted to a dihydrochloride by the addition of an ether solution of hydrogen chloride. Recrystallization from methylene chloride/diethyl ether gave a total of 3.23 g. (52%), m.p. 154°–60° C. The nuclear magnetic resonance and infrared spectra were in agreement with the proposed structure; the material was pure by thin layer chromatography (10% MeOH/CHCl₃).

Analysis Calcd. for $C_{34}H_{52}Cl_2N_2O_4$(MW=623.68): Theory: C, 65.47; H, 8.40; N, 4.49; Found: C, 65.21; H, 8.45; N, 4.47.

EXAMPLE 10

5,5-Dimethyl-10-[3-(piperidino)propionyloxy]-8-pentyl-2-(2-propynyl)-1,2,3,4-tetrahydro-5H-[1]benzopyrano[3,4-d]pyridine tartrate 5,5-Dimethyl-10-hydroxy-8-pentyl-2-(2-propynyl)-1,2,3,4-tetrahydro-5H-[1]benzopyrano[3,4-d]pyridine (1 mm.), dicyclohexylcarbodiimide (1 mm.) and β-piperidinopropionic acid (1 mm.) are combined in 30 ml. of methylene chloride and stirred for 16 hours. The insoluble byproduct of dicyclohexylurea is removed by filtration and the methylene chloride is distilled off using a rotary evaporator. The residue is dissolved in benzene and filtered to remove any insoluble material. The solvent is evaporated and the residue is chromatographed to yield the desired product as neutral material which can be converted to the tartrate by well known methods.

The following compounds are prepared according to the method of Example 10 by reacting the desired benzopyranopyridine with the appropriate acid or acid salt.

EXAMPLE 11

5,5-Dimethyl-8-(3-methyl-2-octyl)-2-(2-propynyl)-1,2,3,4-tetrahydro-10-[4-(thiomorpholino)butyryloxy]-5H-[1]benzopyrano[3,4-d]pyridine hydrobromide Equimolar amounts of 5,5-dimethyl-10-hydroxy-8-(3-methyl-2-octyl)-2-(2-propynyl)-1,2,3,4,-tetrahydro-5H-[1]benzopyrano[3,4-d]pyridine, γ-thiomorpholinobutyric acid hydrobromide and dicyclohexylcarbodiimide are reacted to form the desired product.

EXAMPLE 12

5,5-Dimethyl-2-benzyl-10-[2-(homopiperidino)acetoxy]-8-hexyl-1,2,3,4,-tetrahydro-5H-[1]benzopyrano[3,4-d]pyridine Equimolar amounts of 5,5-dimethyl-2-benzyl-8-hexyl-10-hydroxy-1,2,3,4-tetrahydro-5H-[1]benzopyrano[3,4-d]pyridine, homopiperidinoacetic acid and dicyclohexylcarbodiimide are reacted to form the desired product.

EXAMPLE 13

5,5-Dimethyl-10-[4-(morpholino)butyryloxy]-8-(3-methyl-2-octyl)-2-methyl-1,2,3,4-tetrahydro-5H-[1]benzopyrano[3,4-d]pyridine hydrochloride 5,5-Dimethyl-10-hydroxy-8-(3-methyl-2-octyl)-2-methyl-1,2,3,4-tetrahydro-5H-[1]benzopyrano[3,4-d]pyridine, γ-morpholinobutyric acid hydrochloride and dicyclohexylcarbodiimide are combined in equimolar amounts in methylene chloride and reacted as in Example 1 to give the desired product.

EXAMPLE 14

2-Benzyl-5,5-dimethyl-10-[4-morpholino)butyryloxy]-8-(3-methyl-2-octyl)-1,2,3,4-tetrahydro-5H-[1]benzopyrano[3,4-d]pyridine hydrochloride 2-Benzyl-5,5-dimethyl-10-hydroxy-8-(3-methyl-2-octyl) 1,2,3,4-tetrahydro-5H-[1]benzopyrano[3,4-d]pyridine, γ-morpholinobutyric acid hydrochloride and dicyclohexylcarbodiimide are combined in equimolar amounts in methylene chloride and reacted as in Example 1 to give the desired product.

EXAMPLE 15

2-Benzyl-5,5-dimethyl-10-[4-(2-methylpiperidino)-butyryloxy]8-(1-pentyl)-1,2,3,4-tetrahydro-5H-[1]benzopyrano[3,4-d]pyridine hydrochloride 2-Benzyl-5,5-dimethyl-10-hydroxy-8-(1-pentyl)-1,2,3,4-tetrahydro-5H-[1]benzopyrano[3,4-d]pyridine, γ-(2-methylpiperidino)butyric acid hydrochloride and dicyclohexylcarbodiimide in equimolar amounts are reacted as in Example 1 to give the desired product.

EXAMPLE 16

5,5-Dimethyl-10-[4-pyrrolidino)butyryloxy]-2-phenethyl-8-(2-tetradecyl)-1,2,3,4-tetrahydro-5H-[1]benzopyrano[3,4-d]pyridine hydrochloride 5,5-Dimethyl-10-hydroxy-2-phenethyl-8-(2-tetradecyl)1,2,3,4-tetrahydro-5H-[1]benzopyrano[3,4-d]pyridine, γ-pyrrolidinobutyric acid hydrochloride and dicyclohexylcarbodiimide are reacted in equimolar amounts according to Example 1 to produce the desired product.

EXAMPLE 17

2-Allyl-5,5-diethyl-8-(3-methyl-2-octyl)-10-[4-(piperidino) butyryloxy]-1,2,3,4-tetrahydro-5H-[1]benzopyrano[3,4-d]-pyridine hydrochloride 2-Allyl-5,5-diethyl-8-(3-methyl-2-octyl)-10-hydroxy-1,2,3,4-tetrahydro-5H-[1]-benzopyrano[3,4-d]-pyridine, γ-piperidinobutyric acid hydrochloride and dicyclohexylcarbodiimide are reacted in equimolar amounts to produce the desired product.

EXAMPLE 18

2-(2-Cyclohexylethyl)-5,5-dimethyl-8-(1-pentyl)-10-[5-(morpholino)
valeryloxy]-1,2,3,4-tetrahydro-5H-[1]benzopyrano[3,4-d]pyridine hydrochloride 2-(2-Cyclohexylethyl)-5,5-dimethyl-10-hydroxy-8-(1-pentyl)-1,2,3,4-tetrahydro-5H-[1]benzopyrano[3,4-d]pyridine, δ-piperidinovaleric acid hydrochloride and dicyclohexylcarbodiimide are reacted in equimolar amounts according to Example 1 to form the desired product.

EXAMPLE 19

2-Cinnamyl-8-cyclopropylmethyl-5,5-di(1-propyl)-10-]4-pyrrolidino)
butyryloxy]-1,2,3,4-tetrahydro-5H-~1]benzopyrano[3,4-d]pyridine hydrochloride 2-Cinnamyl-8-cyclopropylmethyl-5,5-di-(1-propyl)10 -hydroxy-1,2,3,4-tetrahydro-5H-[1]benzopyrano[3,4-d]pyridine, γ-pyrrolidinobutyric acid hydrochloride and dicyclohexylcarbodiimide are reacted in equimolar amounts according to Example 1 to form the desired product.

The foregoing detailed description has been given for clearness of understanding only, and no unnecessary limitations should be understood therefrom, as modifications will be obvious to those skilled in the art.

We claim:

1. A compound of the formula

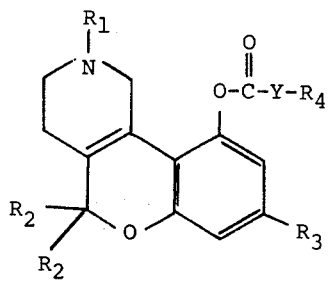

wherein $R_1$ is hydrogen, lower alkyl, lower alkanoyl, cycloalkyl-lower alkyl in which the cycloalkyl has 3 to 8 carbon atoms in the ring, cycloalkyl-lower alkanoyl in which the cycloalkyl has 3 to 8 carbon atoms in the ring, lower alkenyl, lower alkynyl, halo-lower alkenyl, phenyl-lower alkyl, phenyl-lower alkenyl or phenyl-lower alkynyl; $R_2$ is lower alkyl; $R_3$ is an alkyl having one to twenty carbon atoms or is a cycloalkyl-lower alkyl in which the cycloalkyl has 3 to 8 carbon atoms in the ring, Y is a straight or branched chain alkylene having one to eight carbon atoms and $R_4$ is a group of the formula

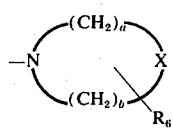

$a$ is an integer from 1 to 4, $b$ is an integer from 1 to 4 and X is $CH_2$, O, S or N—$R_5$, $R_5$ being hydrogen or lower alkyl with the limitation that when X is O, S or N—$R_5$, a and b each must be 2 and $R_6$ is hydrogen or a lower alkyl group bonded to a carbon in the ring; and the pharmaceutically acceptable acid addition salts thereof.

2. A compound in accordance with claim 1, wherein $R_1$is propargyl, each $R_2$ is methyl, $R_3$ is an alkyl group having one to nine carbon atoms, Y is a straight or branched chain alkylene having one to eight carbon atoms, $a$ is 1 or 2, $b$ is 1 or 2 and X is O, S, $CH_2$ or N—$R_5$.

3. A compound according to claim 1 having the name 5,5-dimethyl-10-[4-(piperidino)butyryloxy]-8-(3-methyl-2-octyl)-2-(2-propynyl)-1,2,3,4-tetrahydro-5H-[1]benzopyrano [3,4-d]pyridine or a pharmaceutically acceptable acid addition salt thereof.

4. A compound according to claim 3 having the name 5,5-dimethyl-10-[4-(piperidino)butyryloxy]-8-(3-methyl2-octyl)-2-(2-propynyl)-1,2,3,4-tetrahydro-5H-[1]benzopyrano [3,4-d]pyridine hydrochloride.

5. A compound according to claim 1 having the name 5,5-dimethyl-10-[4-(morpholino)butyryloxy]-8-(3-methyl-2-octyl)-2-(2-propynyl)-1,2,3,4-tetrahydro-5H-[1]benzopyrano [3,4-d]pyridine or a pharmaceutically acceptable acid addition salt thereof.

6. A compound according to claim 5 having the name 5,5-dimethyl-10-[4-(morpholino)butyryloxy]-8-(3-methyl-2-octyl)-2-(2-propynyl)-1,2,3,4-tetrahydro-5H-[1]benzopyrano [3,4-d])pyridine hydrochloride.

7. A compound according to claim 1 having the name 5,5-dimethyl-10-[4-(2-methylpiperidino)butyryloxy]-8-(3-methyl-2-octyl)-2-(2-propynyl)-1,2,3,4-tetrahydro-5H-[1]benzopyrano[3,4-d]pyridine or a pharmaceutically acceptable acid addition salt thereof.

8. A compound according to claim 1 having the name 5,5-dimethyl-10-[5-(piperidino)valeryloxy]-8-(3-methyl-2-octyl)-2-(2-propynl)-1,2,3,4-tetrahydro-5H-[1]benzopyrano [3,4-d]pyridine or a pharmaceutically acceptable acid addition salt thereof.

9. 5,5-dimethyl-10-[4-pyrrolidino)butyryloxy]-8-(3-methyl-2-octyl)-2-(2-propynyl)-1,2,3,4-tetrahydro-5H-[1]benzopyrano[3,4-d]pyridine or a pharmaceutically acceptable acid addition salt thereof.

10. 5,5-dimethyl-10-[4-(piperidino)butyryloxy]-2-(2-propynyl)-8-pentyl-1,2,3,4-tetrahydro-5H-[1]benzopyrano [3,4-d]pyridine or a pharmaceutically acceptable acid addition salt thereof.

11. 5,5-dimethyl-10-[2-methyl-4-(piperidino)-butyryloxy]-8-(3-methyl-2-octyl)-2-(2-propynyl)-1,2,3,4-tetrahydro-5H-[1]benzopyrano[3,4-d]pyridine or a pharmaceutically acceptable acid addition salt thereof.

12. 5,5-dimethyl-10-[3-(piperidino)propionyloxy]-8-pentyl-2-(2-propynyl)-1,2,3,4-tetrahydro-5H-[1]benzopyrano[3,4-d]pyridine or a pharmaceutically acceptable acid addition salt thereof.

13. A compound according to claim 1 in which $R_1$ is a lower alkynyl, each $R_2$ is methyl, $R_3$ is an alkyl having five to nine carbon atoms, Y is a straignt or branched chain alkylene having two to five carbon atoms and, in the groups represented by $R_4$, $a$ and $b$ are the same or different integers from 1 to 3 and $a + b$ is an integer from 3 to 5, $R_6$ is hydrogen or lower alkyl, and X is $CH_2$ or O.

14. A pharmaceutical composition comprising a therapeutically effective amount of a compound of claim 1 and a pharmaceutically acceptable carrier.

15. A pharmaceutical composition in unit dosage form containing about 5 to 300 mg of a compound of claim 1.

16. A pharmaceutical composition according to claim 15 in the form of a tablet.

17. A pharmaceutical composition according to claim 15 in the form of a capsule.

18. A method of relieving pain comprising administering to a patient in pain a therapeutically effective amount of a compound of claim 1.

19. A method of tranquilizing a patient in need of such treatment comprising administering a therapeutically effective amount of a compound of claim 1 to said patient.

20. A method of inducing a sedative-hypnotic effect in a patient which comprises administering to the patient a therapeutically effective amount of a compound of claim 1.

21. A method of inducing an anti-convulsant effect in a patient which comprises administering to the patient a therapeutically effective amount of a compound of claim 1.

* * * * *

UNITED STATES PATENT AND TRADEMARK OFFICE
CERTIFICATE OF CORRECTION

PATENT NO. : 3,991,194

DATED : November 9, 1976

INVENTOR(S) : Louis Selig Harris et al.

It is certified that error appears in the above-identified patent and that said Letters Patent are hereby corrected as shown below:

Column 1, line 52, change "akenyl" to --alkenyl--; column 5, last line, change "258" to --2.58--; column 6, last line, before "5H" insert a dash (-); column 7, line 25, before "2-propynyl" insert a dash (-) and in line 62, before "5H" insert a dash (-); column 8, line 21, and column 11, line 11, before "2-(2-propynyl)" insert a dash (-); column 12, line 38, before "8-(1-pentyl)" insert a dash (-) and in line 52, before "1,2,3,4" insert a dash (-); column 13, line 16, change "]4" to -- [4 --, in line 17, change "⌒1" to -- [1 --, and in line 21, before "10" insert a dash (-); column 14, line 16, before "2-octyl" insert a dash (-).

Signed and Sealed this

Fourth Day of January 1977

[SEAL]

Attest:

RUTH C. MASON
*Attesting Officer*

C. MARSHALL DANN
*Commissioner of Patents and Trademarks*